United States Patent
Wang et al.

[11] Patent Number: 5,804,448
[45] Date of Patent: Sep. 8, 1998

[54] METHOD OF STAINING CELLULAR MATERIAL AND ANALYZING THE SAME

[75] Inventors: Fu-sheng Wang, Claremont; Berend Houwen, Redlands, both of Calif.

[73] Assignee: Toa Medical Electronics Co., Ltd., Hyogo, Japan

[21] Appl. No.: 739,431

[22] Filed: Oct. 29, 1996

[51] Int. Cl.[6] ................................................. G01N 33/48
[52] U.S. Cl. ....................... 436/63; 436/10; 436/17; 436/164; 436/166; 436/172; 436/174; 436/800; 382/133; 382/134; 435/40.5
[58] Field of Search .................... 436/17, 63, 64, 436/164, 166, 171, 172, 174, 800, 10; 435/40.5, 40.51; 356/36, 39, 51; 382/133, 134

[56] References Cited

U.S. PATENT DOCUMENTS

| | | | |
|---|---|---|---|
| 4,893,558 | 1/1990 | Gouch | 101/211 |
| 4,998,284 | 3/1991 | Bacus et al. | 382/133 |
| 5,168,066 | 12/1992 | Zahniser et al. | 436/63 |
| 5,247,339 | 9/1993 | Ogino | 356/73 |
| 5,268,486 | 12/1993 | Waggoner et al. | 548/427 |
| 5,534,416 | 7/1996 | Millard et al. | 436/34 |

FOREIGN PATENT DOCUMENTS 0 601 606 A1  6/1994  European Pat. Off. .

OTHER PUBLICATIONS

"Flow Cytometry and Imaging Device Used in Combination", Fumio Kubota, et al, *Cytometry* 21: 129–132 (1995).

*Primary Examiner*—Maureen M. Wallenhorst
*Attorney, Agent, or Firm*—Bryan Cave LLP

[57] ABSTRACT

A method of staining cellular material where a sample containing the cellular material is stained with a stain solution containing a cyanine dye excitable by infrared rays to contrast its nuclear material from its cytoplasmic material.

8 Claims, 17 Drawing Sheets

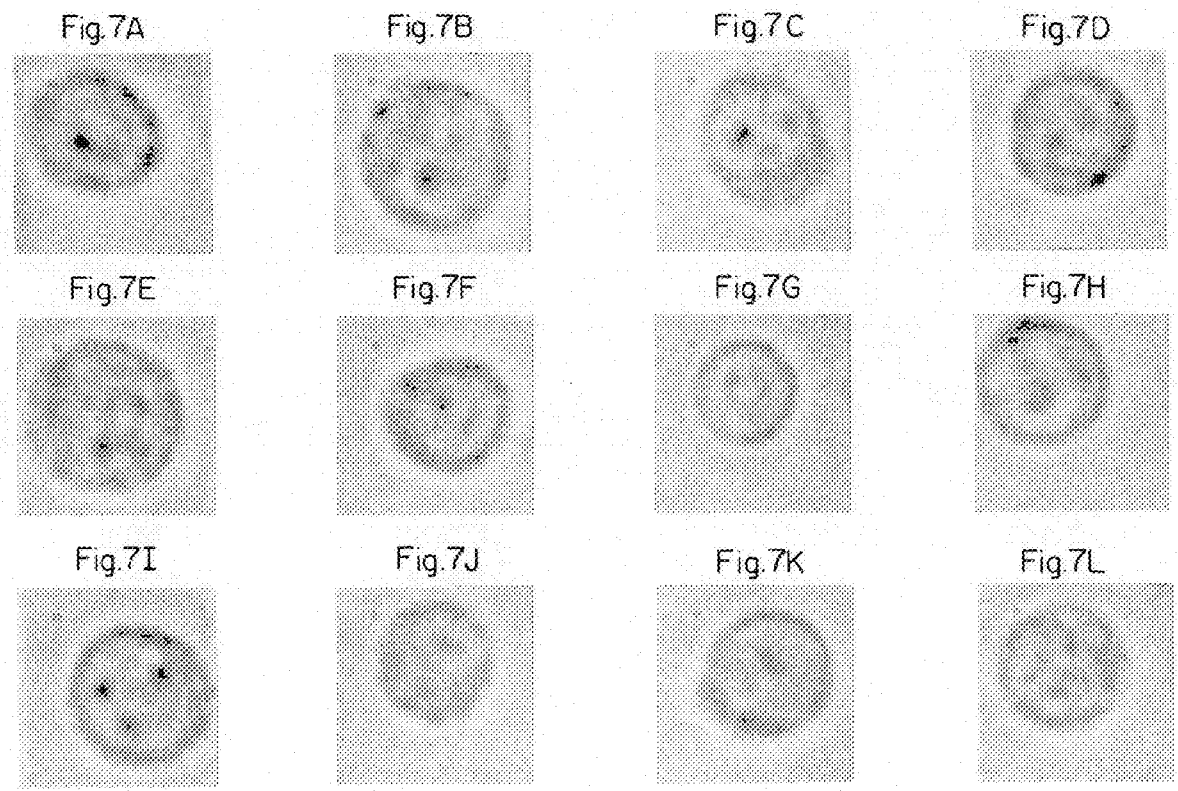

CAM

CONTROL

5,804,448

METHOD OF STAINING CELLULAR MATERIAL AND ANALYZING THE SAME

BACKGROUND OF THE INVENTION

1. Field of the Invention

The present invention relates to a method of staining cellular material for analysis of the same, specifically staining of cellular material for cytological, clinical or biomedical applications using the analysis of cellular material.

2. Description of Related Art

Traditional multicolored stains are desirable for staining cell smears for certain cytological analysis. The stains have a staining pattern in which the nucleus and the cytoplasm of the stained sample are colored differently. Thus they are advantageous for distinguishing cells which are morphologically abnormal or detecting any change after different treatments on the cells. In addition, the variety of colors in such a staining pattern is helpful for reducing eye strain and making diagnoses.

However, the above conventional stains are not suitable for an automated system to analyze cell populations and image or morphology at the same time. Especially, it was impossible to analyze suspended cells with the above conventional stains. Furthermore, most methods using these conventional stains require complicated staining steps just for morphology on slides or cell population analysis with conventional flow cytometer.

On the other hand, new generations of automatic cell analyzers have been developed for achieving observation of cells fixed on a solid carrier such as a slide for cell morphology or cells in a suspended buffer for cell population analysis.

Such analyzers employ flow cytometry or imaging cytometry, for example. The flow cytometry has been widely used in biomedical research including observation on cell surface antigen and cell cycle and is a powerful method to do quantitative study. However, the traditional flow cytometry only provides information of cell population and cannot provide observation of cell morphology simultaneously.

The imaging cytometry is useful for biomedical analysis and some methods thereof have been developed. The methods provide cell morphology or image information, and show cell population on cultured or cyto-spun slides with conventional stainings.

However, the imaging cytometry can not observe suspended cells and none of these methods can perform a large quantity of analysis at a great rate.

In order to image cells more clearly, a method has been proposed which includes staining cellular material with a stain excitable by infrared rays, illuminating the stained cell with energy in infrared spectrum and forming a cell image based on the energy generated by the infrared illumination (U.S. Pat. No. 5,168,066). Specifically, the method includes staining cellular material with Thionine stain, then counterstaining the cellular material, and illuminating the stained cellular material with energy in infrared spectrum. However, this method is also applied only to cell smears on slides, and accordingly it cannot carry out a large quantity of analysis at a great rate.

Then, flow imaging cytometer system (FIC) has been developed to observe simultaneously cell population and cell image in a large amount at a high rate. FIC is a conventional flow cytometer further equipped with a mechanism of pulse imaging [Cytometry, 21: p129–132(1995)]. However, no suitable staining methods for the purpose of observation of cell population and cell image clearly and distinguishing nucleus from cytoplasm clearly were established before the present invention.

SUMMARY OF THE INVENTION

The present invention provides a method of staining the cellular material comprising staining a sample containing cellular material with a stain solution containing a cyanine dye excitable by infrared rays to contrast its nuclear material from its cytoplasmic material.

The present invention also provides a method of analyzing the cellular material comprising staining a sample containing cellular material with a stain solution containing a cyanine dye excitable by infrared rays to contrast its nuclear material from its cytoplasmic material, and then introducing the stained cellular material to a flow imaging cytometer provided with an infrared ray source to obtain cell population information and cell image information.

Optionally, the above methods can be combined with a different type of staining so as to contrast nuclear material from cytoplasmic material as well as observe image of cells with different antigen and in different physiologic and pathologic conditions.

BRIEF DESCRIPTION OF THE DRAWINGS

FIG. 7 is cell images of HL-60 cells stained with HITC in Example 1 of the staining method of the present invention;

DETAILED DESCRIPTION OF THE INVENTION

Figure 1:
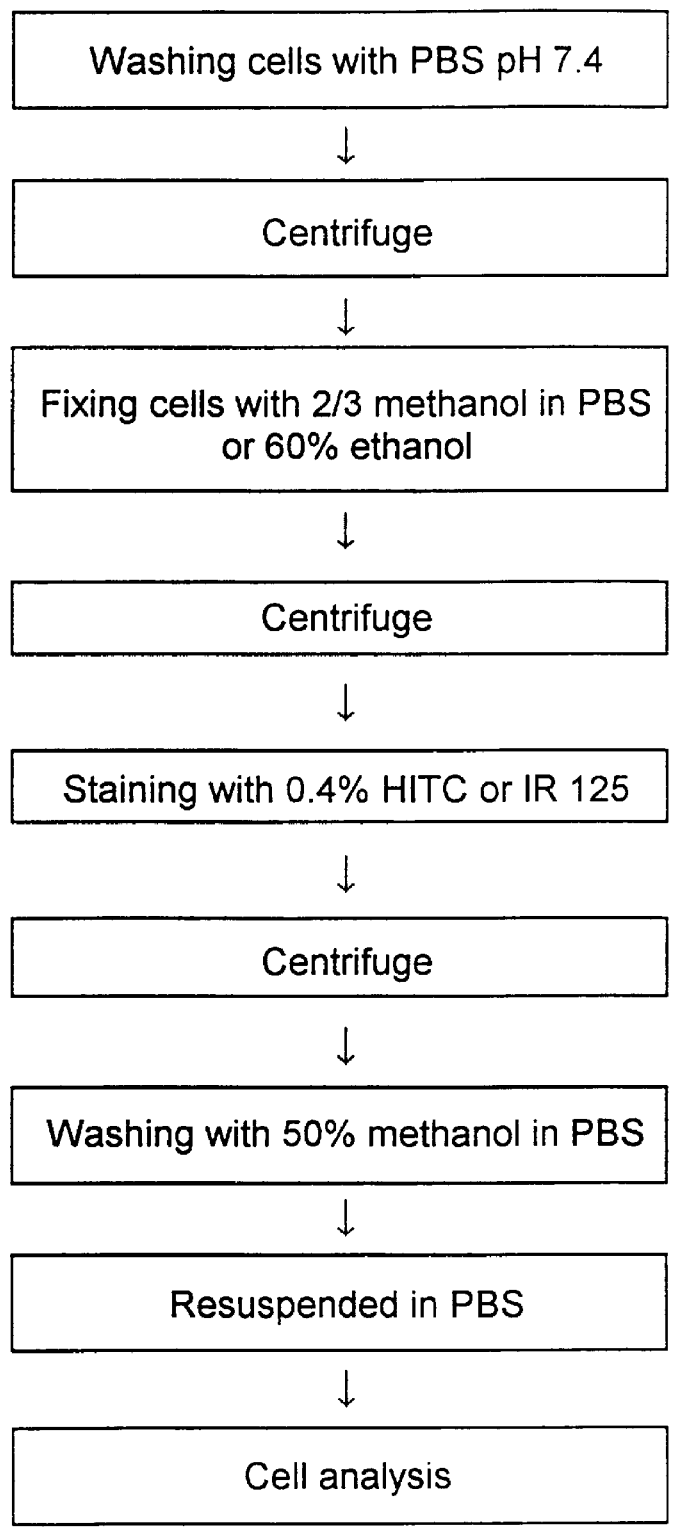
FIG. 1 is a flow chart depicting one staining technique of the present invention.

The method of the present invention provides a staining method aptly used for analyzing a sample containing cellular material at a high speed with accuracy on an analysis systems provided with an infrared ray source. The method can be used for manual analysis and for automated analysis system. The method can also be employed for automatization of a series of analysis steps.

The sample containing cellular material according to the invention means a sample containing any kind of cell comprising cytoplasm and nucleus which are used for cytological, hematological, oncological and clinical purposes, such as peripheral blood cells and urinary cells. Of course, that include cells in physiologic and pathologic condition such as apoptotic cells.

Apoptosis is a word derived from the Greek words apo meaning "off" and ptosis meaning "fall." Thus, it refers to a "falling off," in this case, of cellular viability. It is an active process of gene-directed cellular self destruction and has also been described as programmed cell death, although the distinction has been made between cell death and unscheduled apoptosis. Apoptosis has a hall mark for identification of fragmentation of the cell's DNA via endonucleases. The DNA fragmentation has been being observed under microscope or with electrophoresis and conventional flow cytometer. The staining methods used with the traditional flow cytometer provide information about apoptotic cell population only. Apoptotic cells can generally be derived with Camptothecin (CAM) treatment. For more specific example, the treatment is carried with about 0.1 to 0.8 $\mu$M CAM solution for about 1 to 10 hours.

The cyanine dye excitable by infrared rays means a cyanine dye which can be excited with infrared rays having a wavelength of about 720 to 1500 nm.

The cyanine dye of the present invention can be represented by the formula;

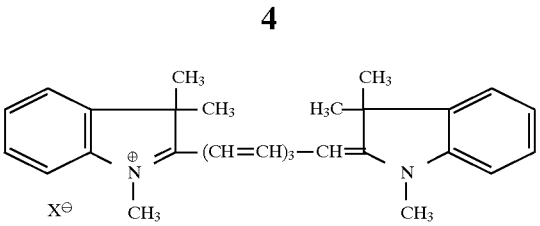

wherein $X^-$ is $ClO_4^-$, $SO_3^-$, $Cl^-$, $F^-$, $Br^-$, $I^-$ or the like, among which, $ClO_4^-$ is preferable, or

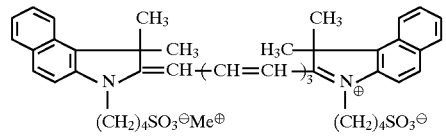

wherein $Me^+$ is $Na^+$, $K^+$ or the like, among which $Na^+$ is preferable.

The preferable cyanine dyes are 1,1',3,3,3', 3'-hexamethylindotricarbocyanine iodide, i.e., 2-[7-(1,3-dihydro-1,3,3-trimethyl-2H-indol-2-ylidene)-1,3,5-heptatrienyl)]-1,3,3-trimethyl-3H-indolium iodide (HITC Iodide), catalog number 08422 and Indocyanine Green, i.e., 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide, inner salt, sodium salt (IR-125), catalog number 09030, from Exciton, Inc., P.O. Box 31126, Overlook Station, Dayton Ohio 45431.

The cyanine dye may be dissolved well in an organic solvent such as lower alkanols, lower alkylene glycols and lower alkylene glycol mono-lower-alkyl ether, examples of which are methanol, ethanol, n-propanol, ethylene glycol and ethylene glycol monoethyl ether, and prepared for use with a concentration of about 0.01 to 1.0 w/v %, preferably about 0.4 w/v % as 2 to 100 ×, preferably about 10 × stock solution to obtain a stain solution.

The stain solution may contain a pH buffer and an additive such as an osmotic pressure compensating agent and a preservative, optionally.

The pH buffer may be a conventional one, examples thereof including Good's buffers such as Tris, MES, BIS-TRIS, ADA, PIPES, ACES, MOPSO, BES, MOPS, TES, HEPES, DIPSO, TAPSO, POPSO, HEPPSO, EPPS, TRICIN, BICINE and TAPS. These pH buffers can be suitably used depending on buffer ability thereof.

Examples of the preservatives are triazine anti-fungus agents and thiazole anti-fungus agents. Examples of the osmotic pressure compensating agents are inorganic acid salts such as sodium chloride and potassium chloride, organic salts such as sodium propionate, and sugars such as mannitol and glucose. These additives can be used in such a concentration that they manifest desired effect and do not affect cellular material to be stained. The pH buffer or the osmotic compensating agent may be separately prepared and stored as aqueous solutions, and mixed with an appropriate quantity of the abovementioned stain solution in use. The preservative when desired is mixed with the above mentioned solution beforehand.

The sample containing cellular material can be stained with the above-described stain solution, for example, by mixing under stirring the sample with the above stain solution, thereby giving good contrast between the nuclear material and the cytoplasmic material. Staining temperature and time are not particularly limited, and are, for example, 15° to 40° C. for 1 to 60 minutes. The sample, before or after being mixed with the stain solution, may be optionally washed, centrifuged and fixed using a saline or a buffer, or a solution which contains saline or a buffer together with about 20 to 60 v/v % organic solvent such as methanol.

In the present invention, the sample may go through a combined staining in which, in addition to the above staining, one or more different types of stainings such as stainings of DNA, stainings with labeled antibodies and stainings with fluorescent dye labeled materials are employed before and/or after the above staining for further distinction of cellular material.

As a dye capable of staining DNA, propidium iodide (PI), EB (ethidium bromide), ethidium-acridine heterodimer, ethidium diazide, ethidium homodimer-1, ethidium homodimer-2, ethidium monoazide, TOTO-1, TO-PRO-1, TOTO-3 and TO-PRO-3 may be used. These dyes are also able to stain nucleic acids or dead cells, and are available from Molecular Probes, Inc. The stain solution containing such dyes may be prepared by dissolving the dye in an organic solvent in a suitable concentration. This stain solution may also contain various additives as described above. Before and/or after the staining with this dye solution, the sample may be washed, centrifuged and fixed optionally at least once.

The cell sample may also be treated with RNAse before or simultaneously with the staining with these dyes.

The labeled antibodies may be commercially available ones which are conventionally used in cyto analysis, such as FITC labeled antibody and PE labeled antibody which are used for the analysis of a tumor-associated surface marker in a hematopoietic organ, cell surface antigen or intracellular antigen, or DNA analysis etc. Also enzyme-labeled antibodies may be used. For FIC analysis, antibodies labeled with a fluorescent dye are preferred. Some other fluorescent dye labeled materials, for example, nucleotides, may also be used.

The sample stained or combined-stained as described above can be introduced to a flow imaging cytometer (FIC) provided with an infrared ray source for obtaining cell population information and cell image information. The FIC with an infrared ray source here is, for example, an apparatus provided with means for obtaining cell image information comprising an infrared ray source with a wavelength of 780 to 1500 nm, an imaging device and an image processor. An example of means for obtaining cell population information is an apparatus provideHd with a visible light source with a wavelength of about 400 to 700 nm, e.g., an argon laser beam, and means for analyzing fluorescence (FL) such as forward fluorescence (FFL), green fluorescence (GFL), orange fluorescence (OFL), and side scattered light (SSC), forward scattered light (FSC) and the like.

In addition to the stainings with HITC or IR-125, the combined stainings with labeled antibodies and TUNEL for apoptosis and potentially any other combination provide methods to see cell image in some special cell populations on a FIC with fast flow rate.

EXAMPLES

The method of staining cellular material according to the invention provides improved contrast of the nucleus from the cytoplasm when the cells are observed on the FIC.

The method is highly effective especially in a FIC with IR laser beam.

Example 1

Cell staining with HITC, IR-125

FIG. 1 shows a cell staining technique in this example. A sample containing one ×10$^6$ HL-60 cells (human promyelocytic leukemia cell available from ATCC) was used. The cells were washed with PBS of pH7.4 and centrifuges at 300 G for 5 minutes. Then the cells were resuspended in one milliliter of PBS and mixed with 2 milliliter of methanol during vortexing. The cells were fixed on ice for 30 minutes and centrifuged at 300 G for 5 minutes. The cells were then resuspended in PBS and mixed with 0.4% HITC or IR-125 solution to make a final concentration of 0.04%. The cells were stained for 30 minutes, then centrifuged and washed with 50% methanol for 10 minutes. After washing, the cells were resuspended in PBS and observed on FIC-2.

FIC-2 is provided with an argon laser with a wavelength of 480 nm at its hemocytometric portion to count cell population. FIC-2 is also provided with a laser with a wavelength of 780 nm at its imaging portion to observe cell morphology. Further FIC-2 is able to display an image at a designated position on a scattergram obtained by the above observation.

Figure 2:
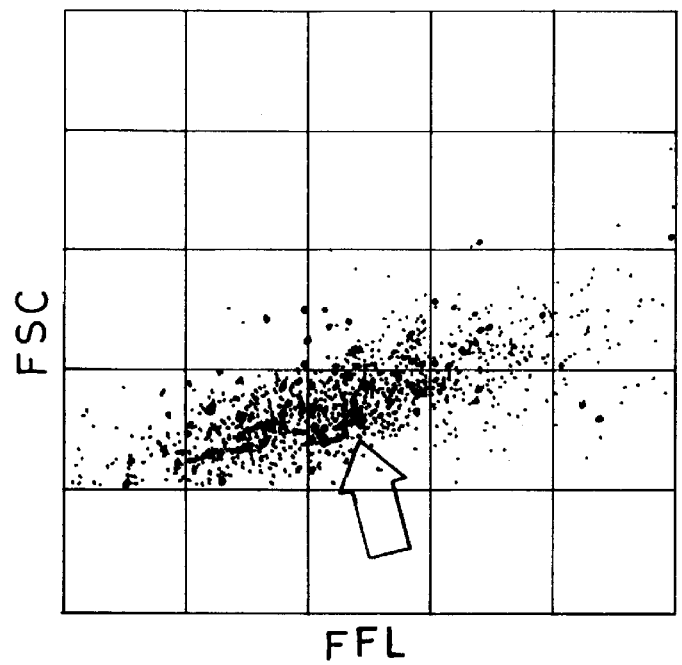
FIG. 2 is a scattergram of FSC and FFL of HL-60 cells stained with IR-125 in Example 1 of the staining method of the present invention.
Figure 3:
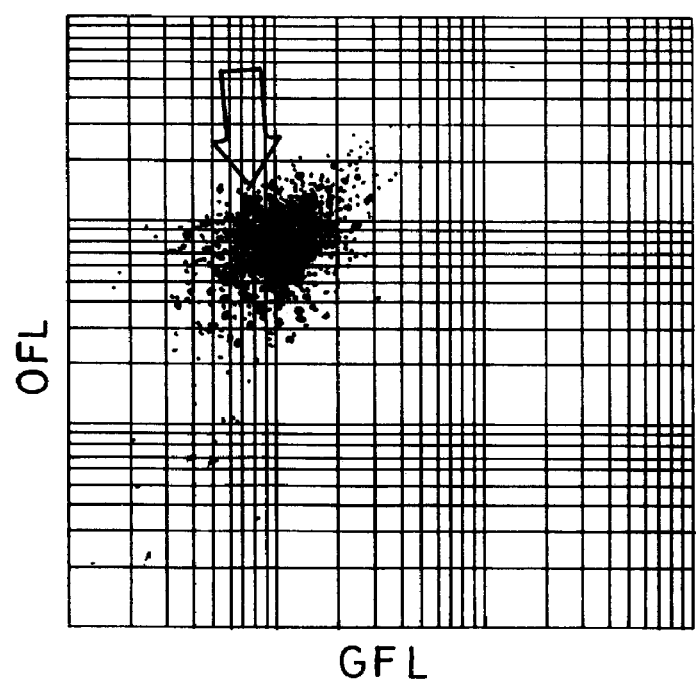
FIG. 3 is a scattergram of OFL and GFL of HL-60 cells stained with IR-125 in Example 1 of the staining method of the present invention.
Figure 4:
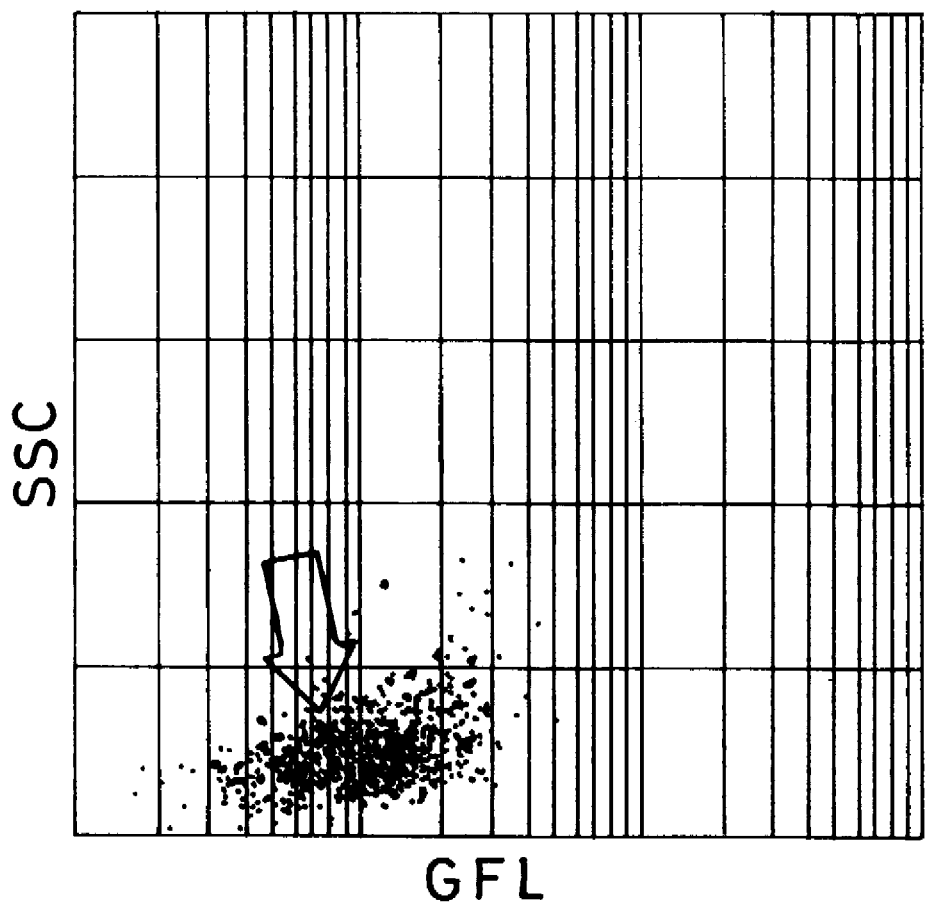
FIG. 4 is a scattergram of SSC and GFL of HL-60 cells stained with IR-125 in Example 1 of the staining method of the present invention.
Figure 5:
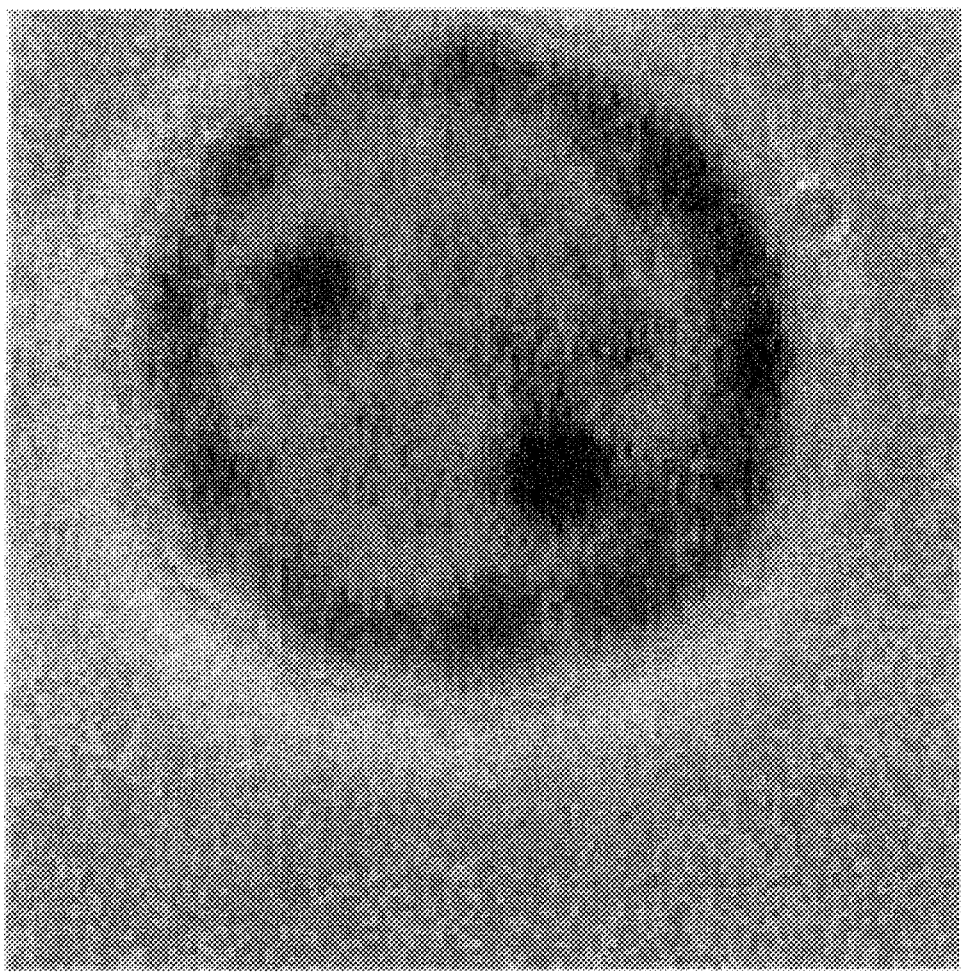
FIG. 5 shows a cell image at the position of X in FIGS. 2 to 4 in Example 1 of the staining method of the present invention.
Figure 6A:
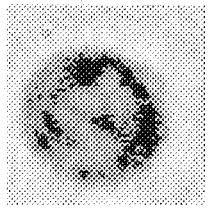
FIG. 6 is cell images of HL-60 cells stained with IR-125 in Example 1 of the staining method of the present invention.
Figure 6B:
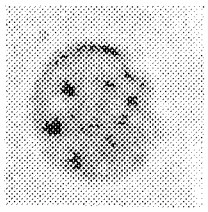
Figure 6C:
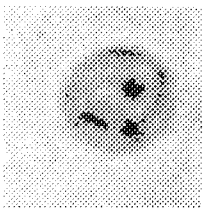
Figure 6D:
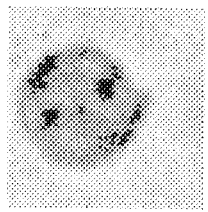
Figure 6E:
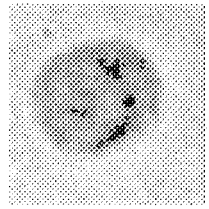
Figure 6F:
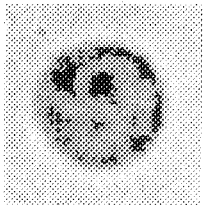
Figure 6G:
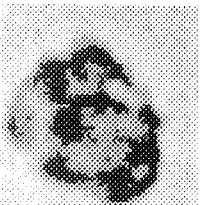
Figure 6H:
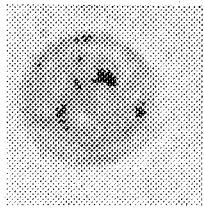
Figure 6I:
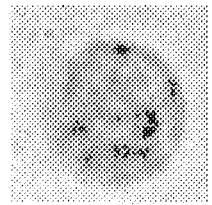
Figure 6J:
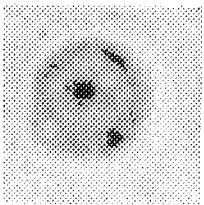
Figure 6K:
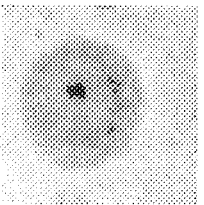
Figure 6L:
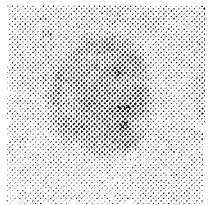
Figure 8A:
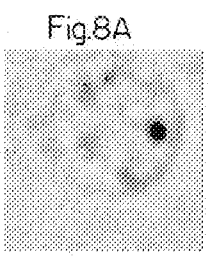
FIG. 8 is cell images of HL-60 cells unstained as control in Example 1 of the staining method of the present invention.
Figure 8B:
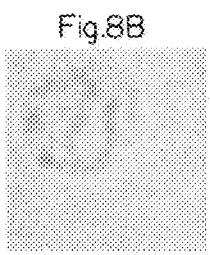
Figure 8C:
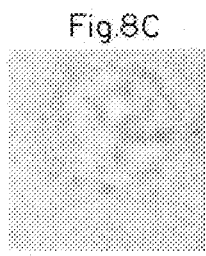
Figure 8D:
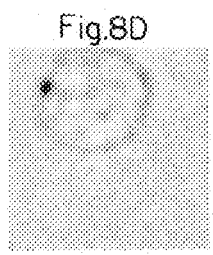
Figure 8E:
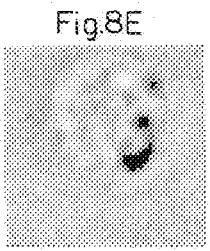
Figure 8F:
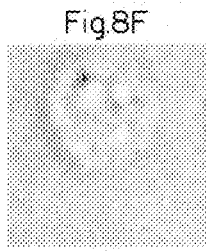
Figure 8G:
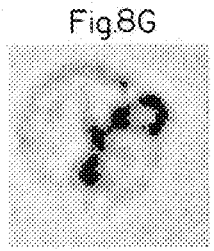
Figure 8H:
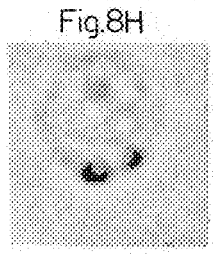
Figure 8I:
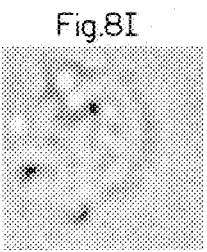
Figure 8J:
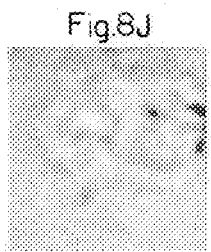
Figure 8K:
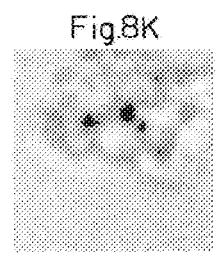
Figure 8L:
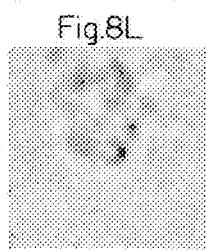

Using this FIC-2, the sample was imaged with image position and focus adjusted and its FFL (whole forwarded fluorescence of 530 nm or more), GFL (fluorescence of 515 to 545 nm), OFL (fluorescence 564 to 606 nm), SSC and/or FSC were observed. The results are shown in figures. FIGS. 2 to 4 show population (distribution) of the cells stained with IR-125 as described above. FIG. 5 shows a cell image at the point of X in FIGS. 2 to 4. FIG. 6 shows stained cell images with IR-125 as described above. FIG. 7 shows images of cells stained with HITC as described above. FIG. 8 shows image of unstained cells as control.

Example 2

Figure 9:
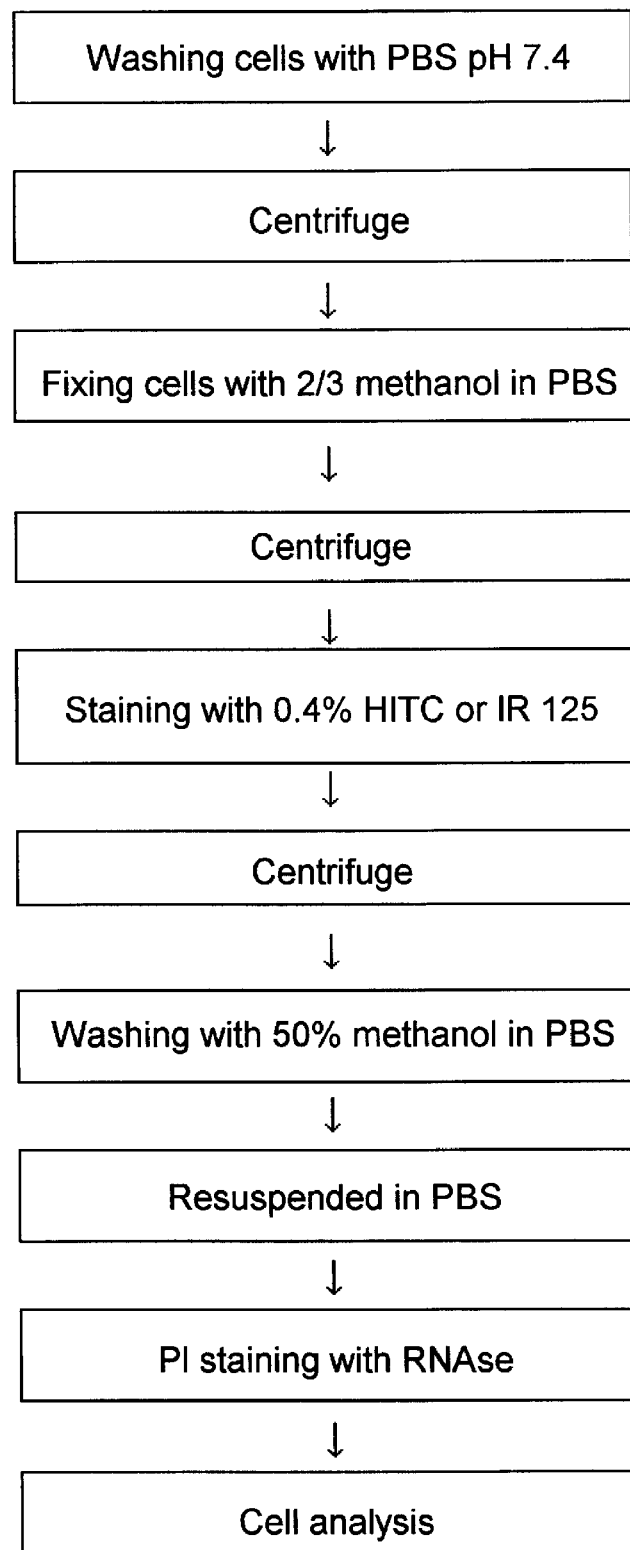
FIG. 9 is a flow chart depicting one combined-staining technique of the present invention.

The cells stained with HITC or IR-125 in Example 1 were fixed, centrifuged as done in Example 1, and then washed with 50% methanol for 10 minutes as shown in FIG. 9. Then some of the cells were further stained with propidium iodide (PI) at 2.5 μg/ml of final concentration and 0.1% of RNAse for 30 minutes.

Example 3

Apoptotic cell observation with HITC and IR-125

To obtain apoptotic cells having a typical morphologic change of cell nuclear fragmentation, HL-60 cells were treated with 0.15 μM of Camptothecin (CAM) for 4 hours. Also cells untreated with CAM was used as control.

These apoptotic cells and normal cells were stained with HITC Iodide in the same manner as described in Example 1 and their cell population and cell morphology were observed simultaneously. The results are shown in FIGS. 10 to 13, and FIGS. 14 to 17 (control), respectively. FIGS. 13 and 17 show cell image at the point of X in FIGS. 10 to 12 and FIGS. 14 to 16, respectively.

Figure 10:
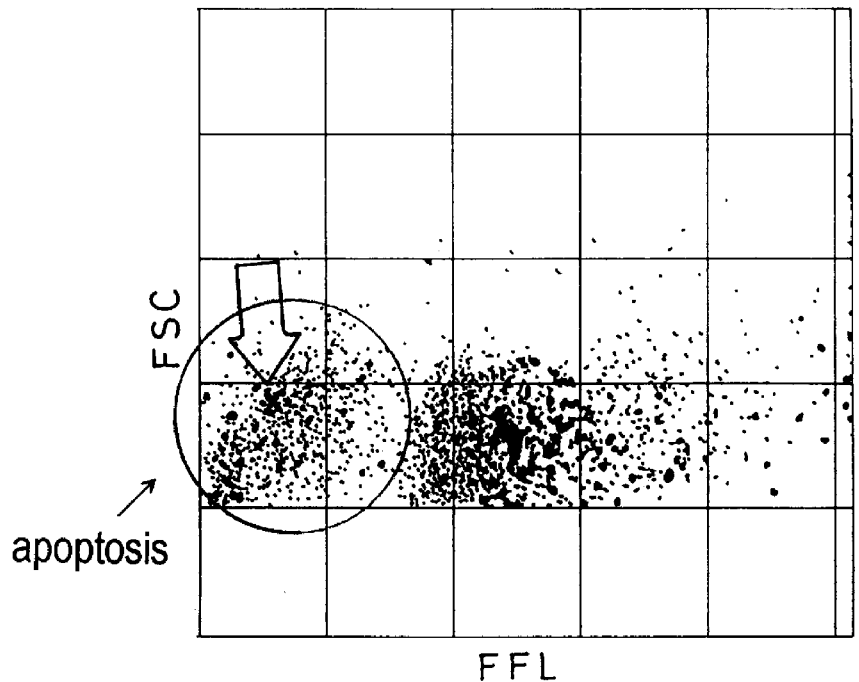
FIG. 10 is a scattergram of FSC and FFL of apoptotic cells stained with HITC in Example 3 of the staining method of the present invention.
Figure 11:
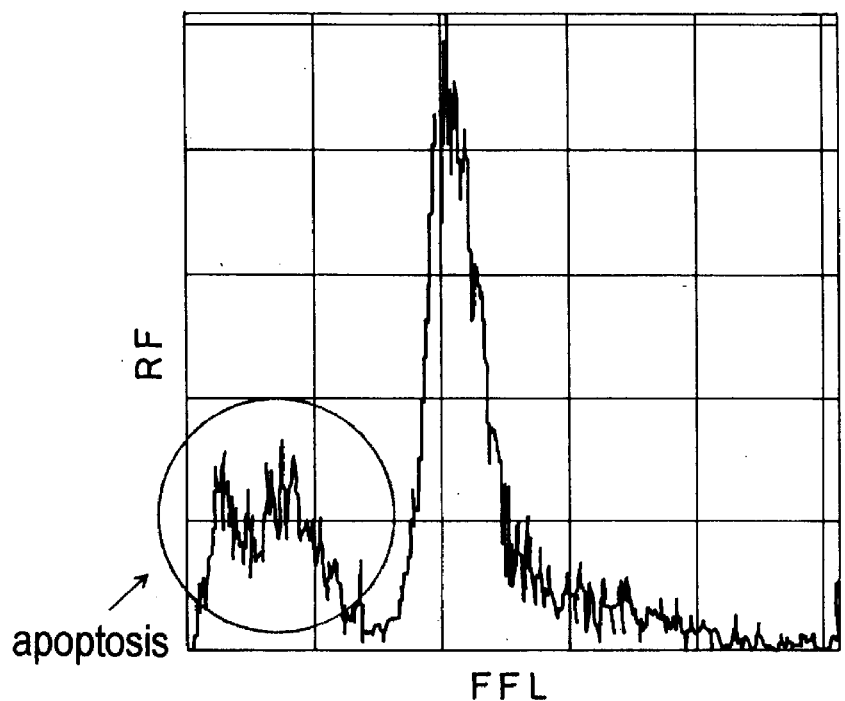
FIG. 11 is a distribution histogram of FFL of apoptotic cells stained with HITC in Example 3 of the staining method of the present invention.
Figure 12:
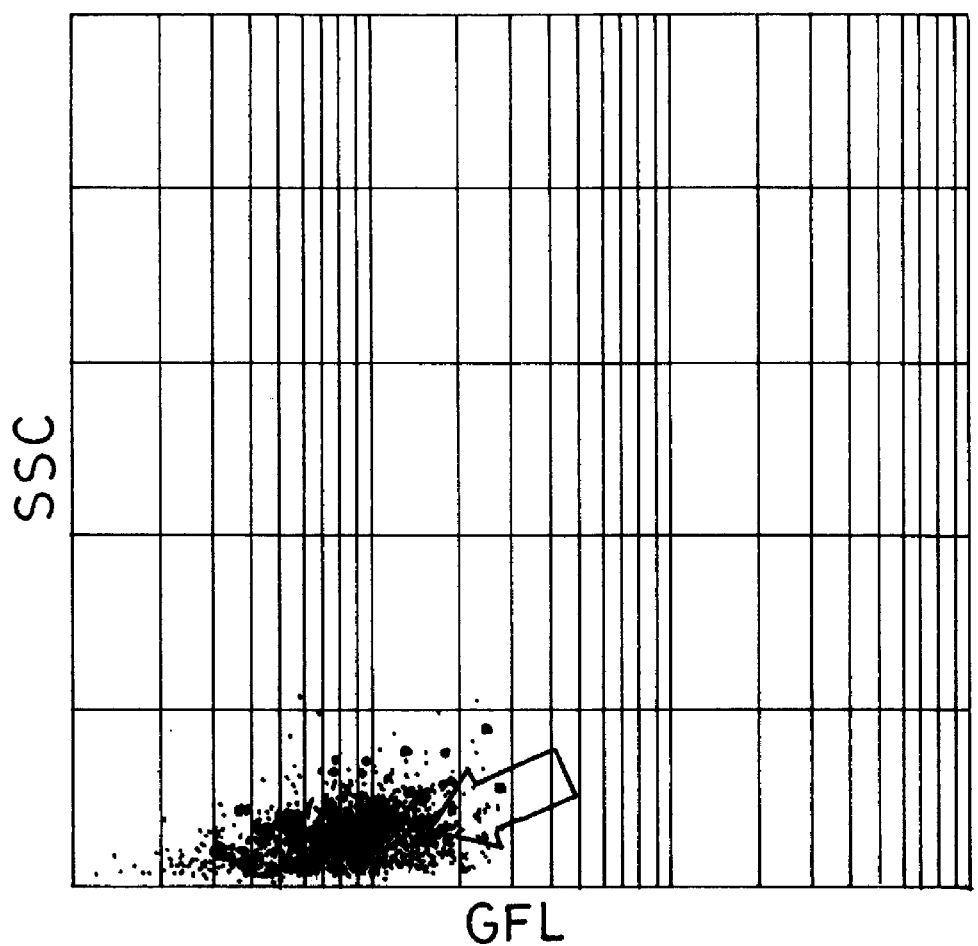
FIG. 12 is a scattergram of SSC and GFL of apoptotic cells stained with HITC in Example 3 of the staining method of the present invention.
Figure 13:
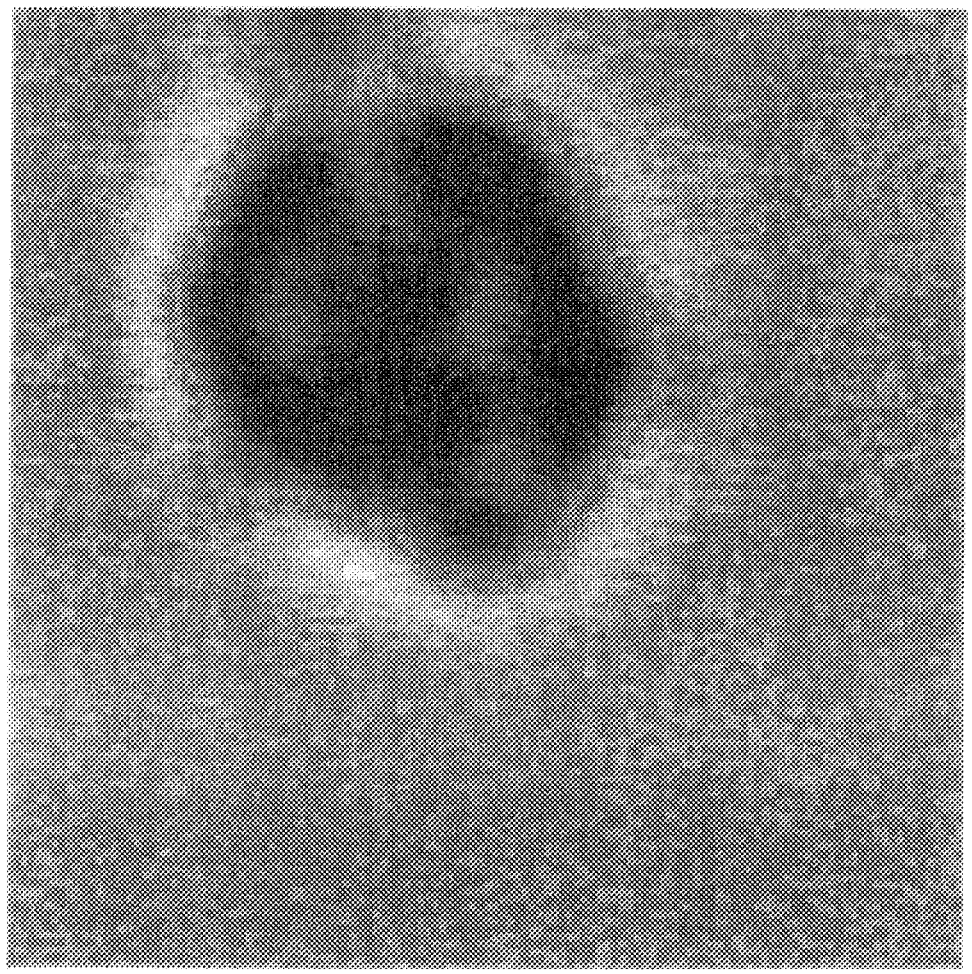
FIG. 13 shows a cell image at the position of X in FIGS. 10 and 12 in Example 3 of the staining method of the present invention.
Figure 14:
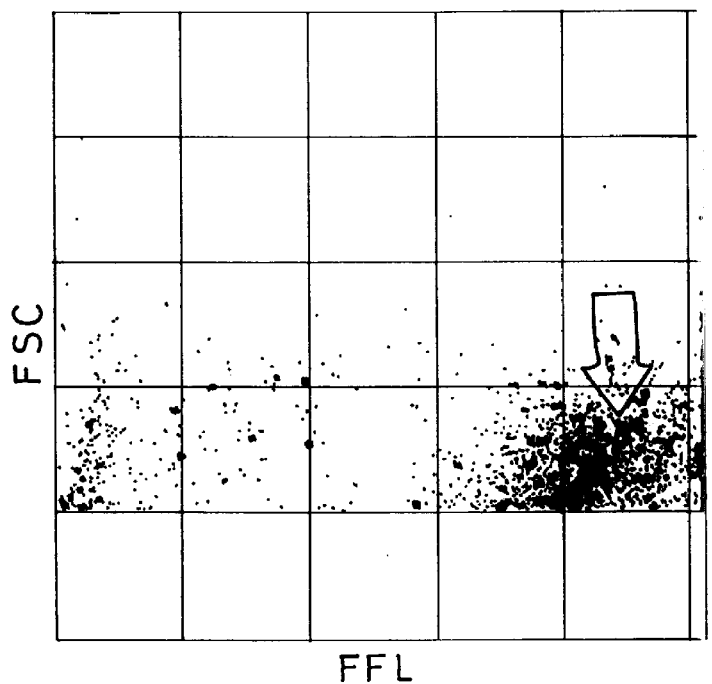
FIG. 14 is a scattergram of FSC and FFL of control cells stained with HITC in Example 3 of the staining method of the present invention.
Figure 15:
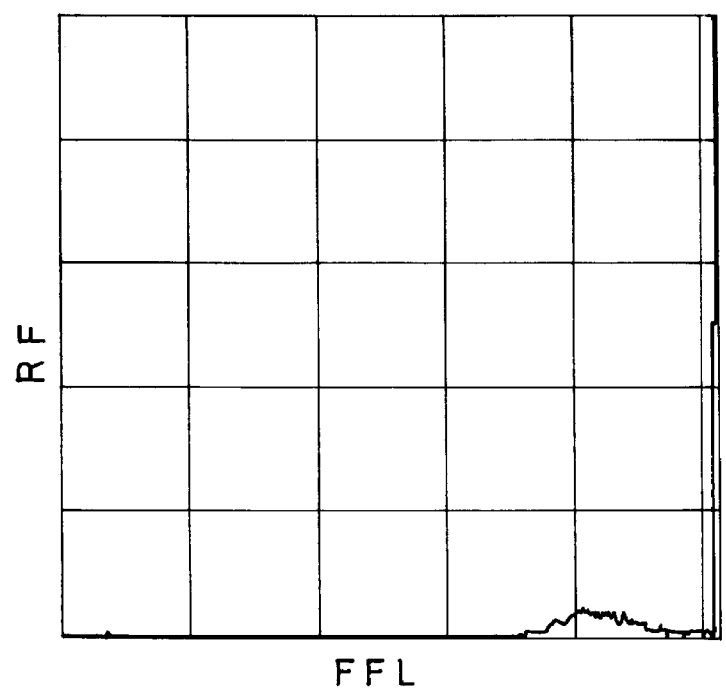
FIG. 15 is a distribution diagram of FFL of control cells stained with HITC in Example 3 of the staining method of the present invention.
Figure 16:
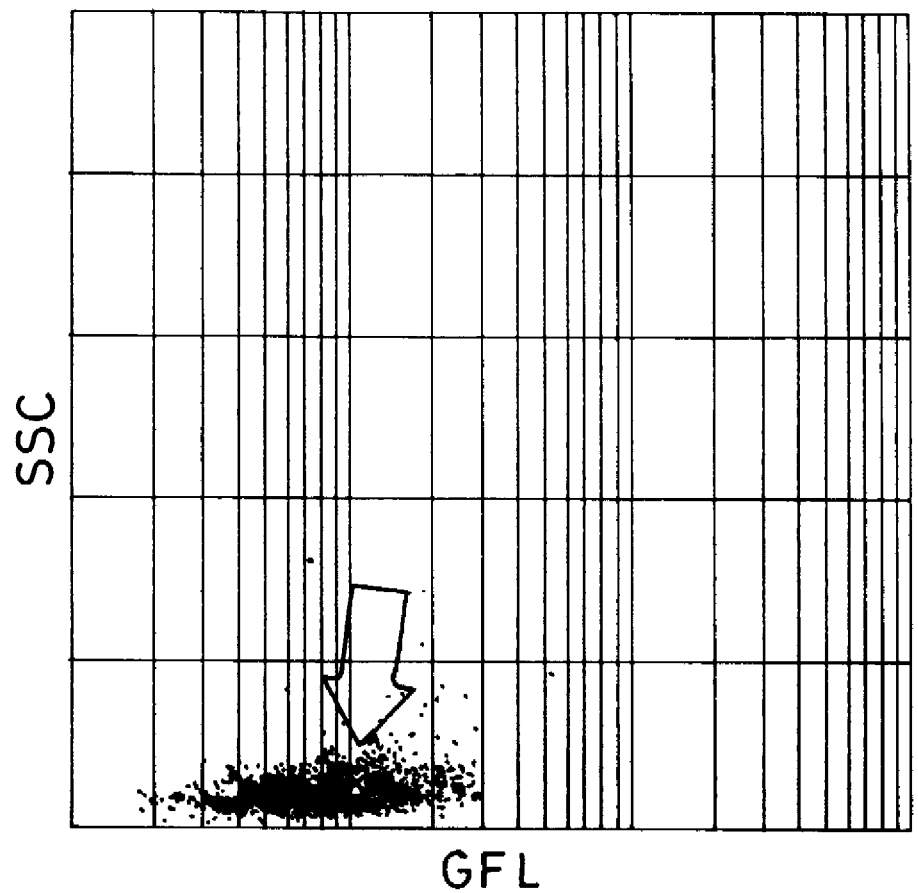
FIG. 16 is a scattergram of SSC and GFL of control cells stained with HITC in Example 3 of the staining method of the present invention.
Figure 17:
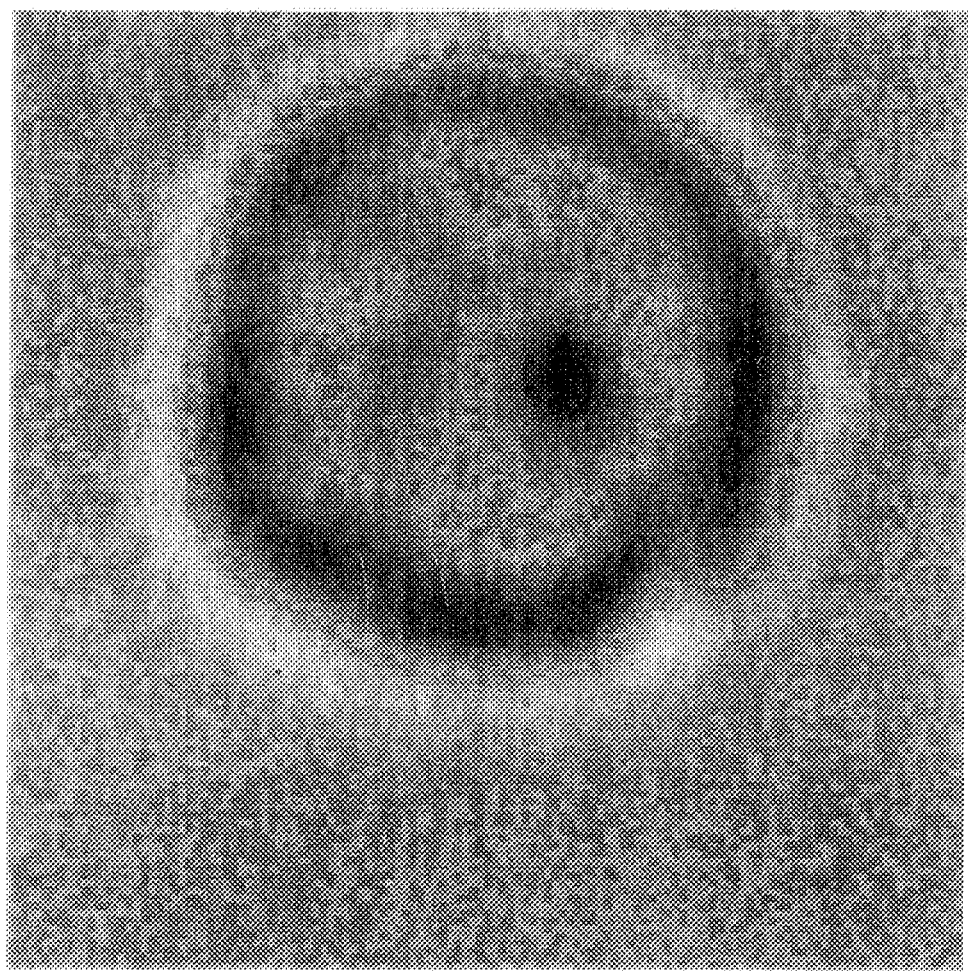
FIG. 17 shows a cell image at the position of X in FIGS. 14 and 16 in Example 3 of the staining method of the present invention.

Referring to FIGS. 10 to 12, cells appeared at lower fluorescence intensity and the distribution was wider, compared with control cell population distribution shown in FIGS. 14 to 16. This result was identical with that on FACScan which will be described later. The image of an apoptotic cell in FIG. 13 shows that the cell had smaller size and multi-fragmented nuclear pieces. On the other hand, the image of a normal cell in FIG. 17 shows that the cell had larger size, one round nucleus and nucleolus. This result was identical with that with Wright-Giemsa-stained cells described later.

Comparative Example 1

Figure 18:
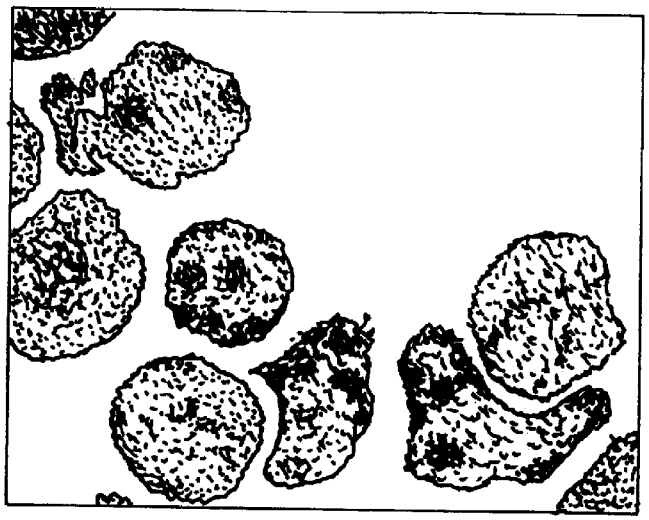
FIG. 18 shows cell morphology of apoptotic cells in Example 3 stained with known Wright-Giemsa stain.
Figure 19:
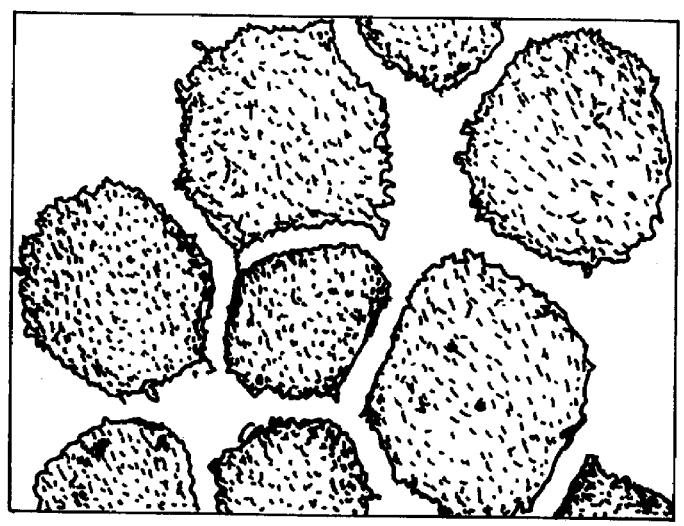
FIG. 19 shows cell morphology of control cells in Example 3 stained with known Wright-Giemsa stain.
Figure 20:
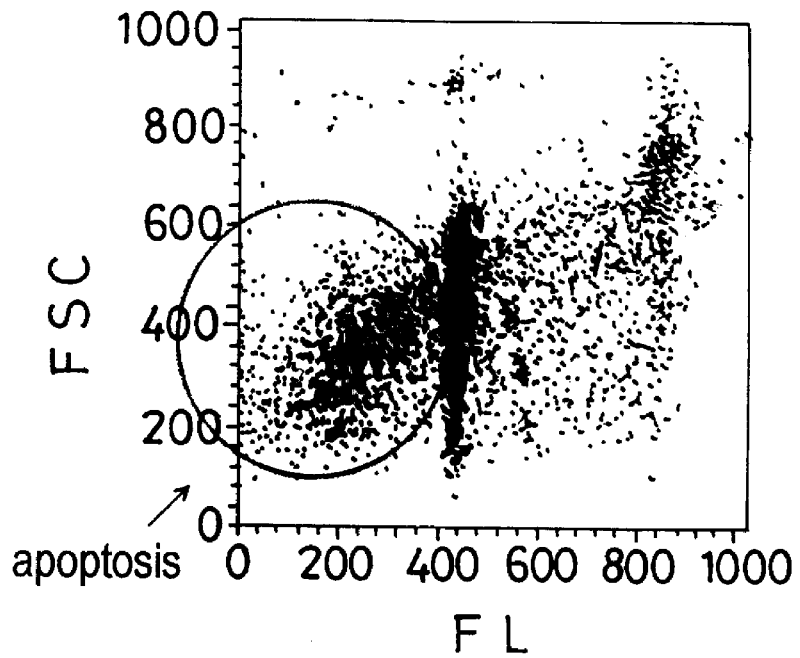
FIG. 20 is a scattergram by FSC and FL1 in FACScan observation of apoptotic cells in Example 3.
Figure 21:
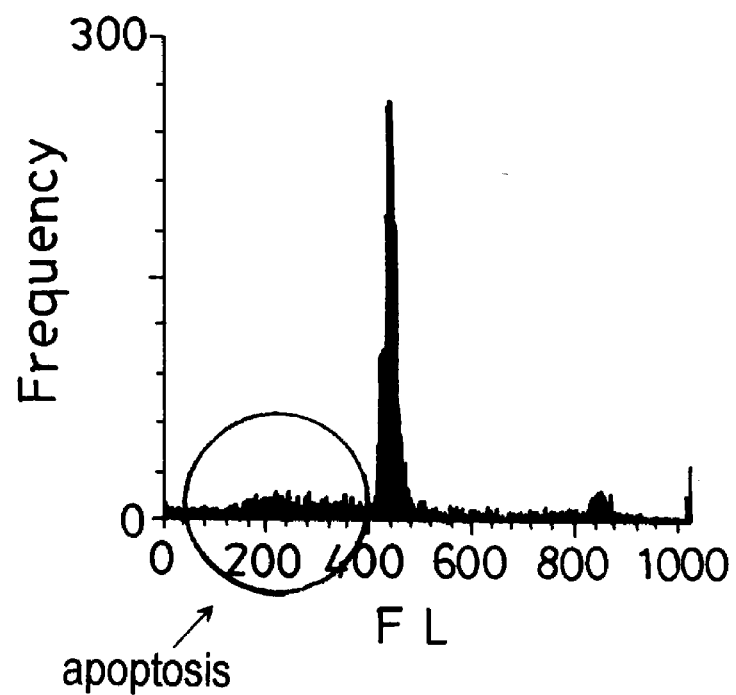
FIG. 21 is a distribution histogram of FL1 in FACScan observation of apoptotic cells in Example 3.
Figure 22:
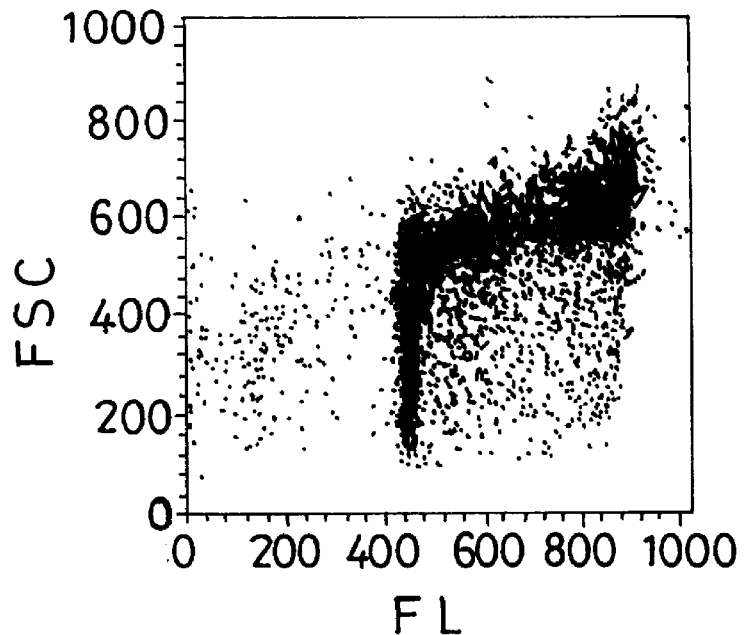
FIG. 22 is a scattergram by FSC and FL1 in FACScan observation of control cells in Example 3.
Figure 23:
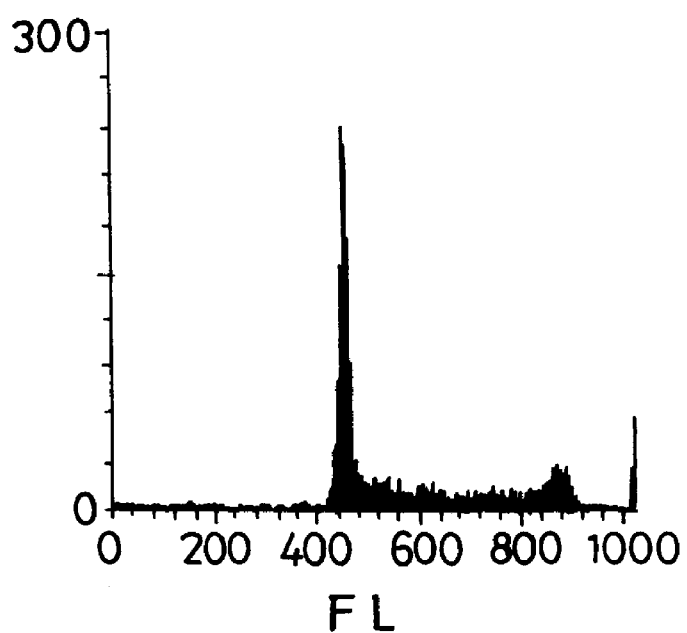
FIG. 23 is a distribution histogram of FL1 in FACScan observation of control cells in Example 3.

The CAM-treated cells and the control cells in Example 3 were Wright-Giemsa-stained in a conventional manner. CAM treated and control cells were cytospun on slides and stained with automatic slide staining machine, Bayer Hematek 2000 with Wright-Giemsa dye. The cells were observed with a Leitz Diaplan microscope. Images were collected with ProgRes 3102 digital video camera and Roche ImageManager 2.2.2, transferred to photoshop 3.0. and printed with Epson ESC P2 color printer. The results are shown in FIGS. 18 and 19. The CAM-treated cells in FIG. 18 shows typical nuclear fragmentation. The cells with fragmented nucleus had condensed nucleus DNA pieces, having apoptosis.

Comparative Example 2

The CAM-treated cells and the control cells in Example 3 were applied to conventional DNA electrophoresis. For DNA electrophoresis, $5 \times 10^6$ cells were washed once with PBS, resuspended in TBE buffer containing 0.25% of Nonident P-40 and 0.1 mg/ml RNAse, incubated at 37° C. for 30 minutes, After then, the cells were incubated another 30 minutes at 37° C. with new added Proteinase K 1 mg/ml. After incubation, 0.1 ml of 6 X loading buffer was added and mixed. The samples were run on 1.5 agarose (GIBCO, catalog number 15510-019) gel at 60 V. Twenty-five $\mu$l tube contents were loaded in each well. One well was loaded with standard marker. The gels were stained with ethidium bromide. The results shows that the cells treated with CAM had typical fragmentation with a band between 200 and 300 base pair. The fragmentation was due to the digestion by endonuclease that was activated by apoptosis process induced by CAM. The result indicated the CAM treatment did induce cell apoptosis.

Comparative Example 3

The CAM-treated cells and the control cells in Example 3 were also observed on FACScan. The results are shown in FIGS. 20 and 21, and FIGS. 22 and 23, respectively. About the apoptotic cell, its population appeared at left side of G 1 population and cells at S phase of cell cycle decreased in number.

Example 4
HITC (or IR-125) staining of peripheral blood on FIC-2

Besides apoptotic research, peripheral blood cell behavior on FIC-2 after the cells were stained with HITC has also been studied. This would be a further shift from basic research to clinical observation. Red blood cell lysing buffer (10 X stock solution)

0.15M NH$_4$Cl 0.8 g 10 mM NaHCO$_3$ 0.084 g 10 mM EDTA (disodium) 0.037 g

H$_2$O 10 ml

The solution was kept at 4° C. for 6 months, and the 10 X solution was diluted to 1 X before use.

(i) To peripheral blood 100 $\mu$l was added 2.5 ml lysing buffer to 100 $\mu$l peripheral blood.

(ii) Gently rocked for 10 minutes.

(iii) Centrifuged at 300 G for 10 minutes.

(iv) Washed twice with PBS.

(v) Resuspended in 0.5 ml PBS, added 0.5 ml of 2% paraformaldehyde and incubated for 10 minutes at room temperature. (modified from Bio-bio res. commun, 201:266, 1994)

(vi) Centrifuged at 300 G at 4° C. for 10 minutes.

(vii) Resuspended in 0.5 ml of cold PBS and added 1 ml of cold methanol.

(viii) Kept 10 minutes on ice.

(ix) Spun and resuspended in 0.9 ml PBS.

(x) Added 0.1 ml of 0.4% HITC in methanol. (FC=0.04%)

(xi) Kept at room temperature for 30 minutes.

(xii) Spun at 300 G for 10 minutes.

(xiii) Washed with 50% methanol for 10 min. Washed with cold PBS.

(xiv) Resuspended in 100 $\mu$l PBS solution containing 0.5% BSA and 0.1% RNAse.

(xv) Washed once.

(xvi) Optionally filtered cells with 30 nm filter.

(xvii) Tested on FIC-2 with dilute by 100 times, 300 sec. and flashed all cells.

The structure of cells unstained with HITC was not seen in a sufficiently clear way, and the type of the cells was not distinct. On the other hand, the structure of cells stained with HITC was clearly seen, and especially lymphocytes and granulocytes were observed to have typical cell structures.

According to the staining method of the present invention, not only cell image information but also cell population information can be simultaneously obtained in analysis of samples, and thus the present invention has great possibility in cytological, hematological, oncological, and biological applications.

In apoptosis research and clinical observation, the present invention can be utilized for detecting morphologic change by examining their images during they are detected having abnormal population by the cytometric portion. The information both cell population and image obtained in the method of the present invention can also be utilized for new drug evaluation in vitro drug sensitivity assay of cancer patient, cell death physiology and pathology as well as other related researches.

Further, the present invention, combined with other staining can raise reliability in the distinction of apoptotic cells from pseudoapoptotic cells with examination of obtained images while the distinction cannot be done by the conventional analysis only by use of flow cytometry.

What is claimed is:

1. A method of staining cellular material comprising staining a sample containing cellular material with a stain solution containing a cyanine dye excitable by infrared rays to contrast cellular nuclear material from cellular cytoplasmic material wherein the cyanine dye is selected from the group consisting of dyes having tie formulae:

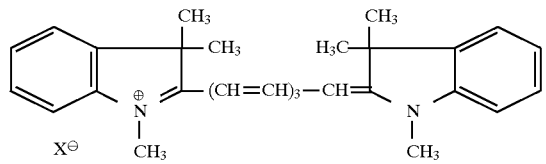

wherein X$^-$ is ClO$_4^-$, SO$_3^-$, Cl$^-$, F$^-$, Br$^-$, or I$^-$; and

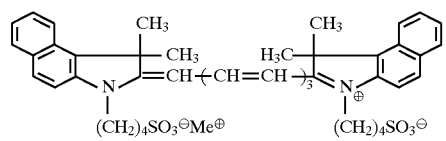

wherein Me$^+$ is Na$^+$ or K$^+$.

2. The method of staining cellular material according to claim 1 wherein the sample containing cellular material contains apoptotic cells or peripheral blood cells.

3. The method of staining cellular material according to claim 1, which further comprises a combined staining of the cellular material.

4. The method of staining cellular material according to claim 3 wherein the combined staining is either one or both of a staining of the cellular material with labeled-antibody and a staining of DNA in addition to the staining of the cellular material with the cyanine dye.

5. The method of staining cellular material according to claim 1 wherein the stain solution comprises 1,1', 3,3,3', 3'-hexamethylindotricarbocyanine iodide or Indocyanine Green as the cyanine dye, an organic solvent and a pH buffer.

6. A method of analyzing cellular material comprising staining a sample containing cellular material with a stain solution containing a cyanine dye excitable by infrared rays to contrast cellular nuclear material from cellular cytoplasmic material, and introducing the stained cellular material to a flow imaging cytometer provided with an infrared ray source to obtain cell population information and cell image information wherein the cyanine dye is selected from the group consisting of dyes having the formulae:

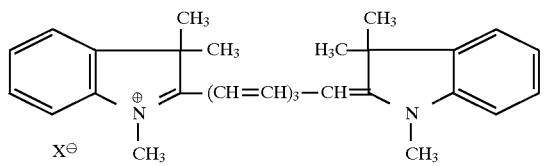

wherein $X^-$ is $ClO_4^-$, $SO_3^-$, $Cl^-$, $F^-$, $Br^-$, or $I^-$; and

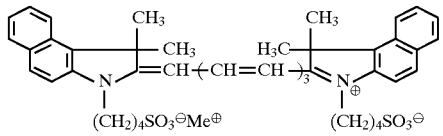

wherein $Me^+$ is $Na^+$ or $K^+$.

7. A method of analyzing cellular material comprising staining a sample containing cellular material with a stain solution containing a cyanine dye excitable by infrared rays in combination with a combined staining so as to contrast cellular nuclear material from cellular cytoplasmic material as well as to observe images of cells with different antigen and under different physiologic and pathologic conditions, and introducing the stained cellular material to a flow imaging cytometer provided with an infrared ray source to obtain cell population information and cell image information wherein the cyanine dye is selected from the group consisting of dyes having the formulae:

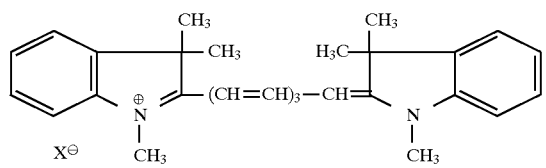

wherein $X^-$ is $ClO_4^-$, $SO_3^-$, $Cl^-$, $F^-$, $Br^-$, or $I^-$; and

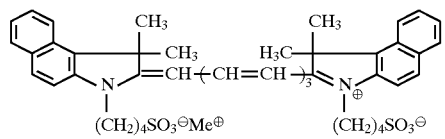

wherein $Me^+$ is $Na^+$ or $K^+$.

8. The method of analyzing cellular material according to claim 7, wherein the combined staining is a either one or both of a staining of the cellular material with labeled-antibody and a staining of DNA in addition to the staining of the cellular material with the cyanine dye.

* * * * *